(12) United States Patent
Yang et al.

(10) Patent No.: US 6,413,396 B1
(45) Date of Patent: Jul. 2, 2002

(54) ENZYME ELECTRODE SENSOR AND MANUFACTURING METHOD THEREOF

(75) Inventors: Haesik Yang; Youn Tae Kim, both of Taejon (KR)

(73) Assignee: Electronics and Telecommunications Research Institute, Taejon (KR)

(*) Notice: Subject to any disclaimer, the term of this patent is extended or adjusted under 35 U.S.C. 154(b) by 0 days.

(21) Appl. No.: 09/497,883

(22) Filed: Feb. 4, 2000

(30) Foreign Application Priority Data

Dec. 27, 1999 (KR) .............................. 99-62430

(51) Int. Cl.[7] .............................. G01N 27/26
(52) U.S. Cl. ........................ 204/403; 204/4.18
(58) Field of Search ................... 204/403, 418

(56) References Cited

U.S. PATENT DOCUMENTS

| | | | |
|---|---|---|---|
| 5,286,364 A | 2/1994 | Yacynych et al. | 204/418 |
| 5,352,348 A | 10/1994 | Young et al. | 204/153.12 |
| 5,354,447 A | * 10/1994 | Uenoyama et al. | 204/403 |
| 5,356,786 A | 10/1994 | Heller et al. | 435/14 |
| 5,391,250 A | 2/1995 | Cheney, II et al. | 156/268 |
| 5,422,246 A | 6/1995 | Koopal et al. | 435/14 |
| 5,540,828 A | 7/1996 | Yacynych | 204/418 |
| 5,624,537 A | 4/1997 | Turner et al. | 204/403 |
| 5,776,324 A | 7/1998 | Usala | 204/403 |
| 5,795,774 A | 8/1998 | Matsumoto et al. | 435/287.9 |
| 5,804,048 A | 9/1998 | Wong et al. | 204/403 |
| 6,063,259 A | * 5/2000 | Wang et al. | 205/777.5 |
| 6,156,173 A | * 12/2000 | Gotoh et al. | 204/403 |

OTHER PUBLICATIONS

Bindra et al., "Design and In Vitro Studies of a Needle–Type Glucose Sensor for Subcutaneous Monitoring," *Analytical Chemistry* 63(17):1692–1696, 1991. month unknown.

Zhang et al., "Elimination of the Acetaminophen Interference in an Implantable Glucose Sensor," *Analytical Chemistry* 66(7):1183–1188, Apr. 1994.

Murphy, Lindy J., "Reduction of Interference Response at a Hydrogen Peroxide Detecting Electrode Using Electropolymerized Films of Substituted Naphthalenes," *Analytical Chemistry* 70(14):2928–2935, Jul. 1998.

Matsumoto et al., "A Micro–Planar Amperometric Glucose Sensor Unsusceptible to Interference Species," *Sensors and Actuators B 49*, pp. 68–72, 1998, month unknown.

Yang et al., "Development of Needle–Type Glucose Sensor With High Selectivity," *Sensors and Actuators B 46*, pp. 249–256, 1998.

* cited by examiner

Primary Examiner—T. Tung
Assistant Examiner—Alex Noguerola
(74) Attorney, Agent, or Firm—Seed IP Law Group PLLC

(57) ABSTRACT

An enzyme electrode sensor and a fabricating method thereof, and more particularly, an enzyme electrode sensor which is a biosensor using electrochemical measurement and a manufacturing method thereof. The sensor includes an electrode, a first nonconducting polymer layer formed by electropolymerization outside the electrode wherein enzyme is immobilized in the nonconducting polymer layer, a second nonconducting polymer layer in which enzyme is not immobilized, the second nonconducting layer formed by electropolymerization outside the first nonconducting polymer layer, and an outer layer formed outside the second nonconducting layer. The sensor selectivity is improved as the interference of organic materials is inhibited, and the interference of acetaminophen causing the major problem with a glucose sensor is controlled effectively by the sensor.

6 Claims, 3 Drawing Sheets 11  12  13  14

ENZYME ELECTRODE SENSOR AND MANUFACTURING METHOD THEREOF

TECHNICAL FIELD

The present invention relates to an enzyme electrode sensor and a fabricating method thereof, and more particularly, to an enzyme electrode sensor which is a biosensor using electrochemical measurement and a manufacturing method thereof.

BACKGROUND OF THE INVENTION

Research has focused on developing a multi-functional small-sized sensor, e.g., a biosensor of which selectivity is excellent, and of which precision is excellent as health and environment become personal major concerns.

A biosensor introducing enzyme and electrochemical measurement has been developed widely. In this case, the enzyme includes glucose oxidase, lactate oxidase, alcohol oxidase, cholesterol oxidase, and the like.

A glucose sensor of the enzyme electrode sensors prevails in the study for analyzing blood sugar levels of a diabetic by measuring the concentration of glucose.

Glucose oxidase of an oxidative type in the glucose sensor transforms the glucose into gluconic acid which is reduced. This reduced glucose oxidase reacts with oxygen dissolved in a solution or electron-transferring medium, thereby generating $H_2O_2$ or being transformed into the oxidized type again by reducing the electron-transferring medium.

The hydrogen peroxide or the reduced electron-transferring medium generated from the above reaction may be oxidized into oxygen or oxidized electron-transferring medium, as shown in reaction formula 1 and reaction formula 2, by an electrode of Pt, Rh or the like.

Reaction formula 1:

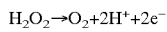

$$H_2O_2 \rightarrow O_2 + 2H^+ + 2e^-$$

Reaction formula 2:

electron-transferring medium(reduced type)→electron-transferring medium(oxidized type)+$e^-$ A glucose sensor measures the concentration of glucose by measuring the oxidation current of hydrogen peroxide, the other oxidation current of the reduced electron-mediator, the concentration change of oxygen due to the reaction by which oxygen is reduced to hydrogen peroxide, or the pH change caused by gluconic acid.

The measurement of oxidizing current of hydrogen peroxide is widely used out of the four measuring methods.

An enzyme electrode measuring the oxidation current of hydrogen peroxide generally consists of several layers, mainly divided into an inner layer and an outer layer.

The inner layer of the enzyme electrode plays roles such as immobilization of enzyme, reduction of interference of organic compounds, and prevention of electrode fouling or poisoning. If the layer consists of only the inner layer without the outer layer, the current change according to the concentration of glucose depends highly on the kinetics of the enzyme reaction thereby failing to show a linear relationship in a wide range of concentration.

On the other hand, provided that an inner layer is coated with an outer layer obstructing the migration of glucose, the migration of glucose takes place slowly. Therefore, current change according to the glucose concentration becomes more linear. One of polyurethane, cellulose acetate, Nafion, Teflon, Kel-F and the like may be used as the substance of the outer layer.

Glucose concentration in human blood is 2 to 30 mM, while oxygen concentration is 0.02 to 0.2 mM. Under such circumstances as extremely low concentration of oxygen, the oxidation current of hydrogen peroxide depends on the oxygen concentration, not the glucose concentration. Thus, a layer slowing down the diffusion of glucose as well as supplying oxygen is needed. The outer layer may fulfill this requirement.

Moreover, the outer layer also prevents the current change due to agitation of a solution. And, the outer layer, when used built-in or attached-to a human body, consists of the outer layer which is coated with a bio-affinity substance layer.

One method of fixing enzyme to the inner layer includes the step of fixing the enzyme when the layer is formed by dip coating or spin coating or fixing the enzyme before or after the formation of the layer.

A method of forming a layer by use of electropolymerization enables control of the thickness of the layer as well as the formation of a very thin layer. On the other hand, another method of forming a layer by use of dip coating, spin coating, or dispensing has the difficulty of controlling the thickness of the layer, thereby forming a relatively thick layer Therefore, electropolymerization is very effective for the reproducible formation of a layer.

When an inner layer is formed by electropolymerization without the enzyme, the enzyme should be immobilized on the layer by dip coating, spin coating, or dispensing.

Enzyme should be fixed to a layer by dip coating or spin coating provided that the enzyme is to be fixed to a polymer layer having been formed by electrochemical polymerization.

A method of fabricating a chemical sensor and a biosensor is disclosed in U.S. Pat. No. 5,540,828 which teaches that a polymer layer formed on an electrode by electrochemical polymerization is coated with chemicals or bio-substances for sensing or that a non-electrically-conductive polymer layer is formed thereon after an electrode has been coated with chemicals or bio-substances for sensing. The method enables to fabricate a sensor with ease provided that a relatively large electrode is used for the fabrication.

Unfortunately, in the case of microarray electrodes that analyze various substances simultaneously, the method has the difficulty of immobilizing different enzymes or biomaterials on each electrode by dip coating or spin coating.

Moreover, as a surface of the electrode is coated with non-electrically-conductive enzyme, the polymer layer is unable to grow well as well as a sensing substance has difficulty in reaching the enzyme through the polymer layer into which obstructive substances are hard to penetrate.

Accordingly, the most effective method of forming an inner layer of a micro-array electrode is that a polymer layer is formed by electrochemical polymerization as soon as enzyme is fixed thereon.

In order to grow such a polymer layer on an electrode by electropolymerization, the polymer layer should have high electric conductivity.

An electrically-conductive polymer such as polypyrrole has very high electric conductivity, thereby growing well. Yet, when an inner layer is formed of polypyrrole, interference of obstructive substances plays a great role therebetween due to its easy penetration into the inner layer. Besides, background current is too large and variation according to time fluctuates greatly since it is hard to eliminate electrochemical activation of the polypyrrole inner layer.

A layer of electro-polymerized nonconducting polymer, which is formed by using monomers such as phenylenediamine, aminohydroxybenzene, dihydroxybenzene, diaminonaphthalene, aminohydroxynaphthalene, dihydroxynaphthalene or the like, grows for a while but stop growing due to its low electric conductivity.

However, obstructive substances are hard to pass through a nonconducting polymer layer made of poly(meta-phenylenediamine) or the like, even though the polymer layer is very thin, thereby reducing the interference of the obstructive substances and background current in a neutral solution providing no electrochemical activation.

Interference has been the major problem in developing such enzyme electrode sensors, oxidize hydrogen peroxide, a high voltage of +650 mV should be applied to a Pt electrode vs. an Ag/AgCl reference electrode. At that voltage level, some organic metabolites, such as ascorbic acid, acetaminophen, uric acid, and the like are easily oxidized.

Even though hydrogen peroxide results from the selective reaction between an enzyme and analyte, sensor selectivity is low if the oxidation of organic materials on a Pt electrode is considerable. That's why a layer, which blocks the diffusion of interferents but lets hydrogen peroxide pass through, is required thereof.

A glucose sensor, which comprises an outer layer supplying oxygen sufficiently, but retarding the diffusion of glucose and an inner layer inhibiting the diffusion of interferents to an electrode wherein glucose oxidase is present between the outer and inner layers, is disclosed in U.S. Pat. No. 5,804,048. Such a method is easily accomplished with a relatively large electrode but is hard to apply to a microsensor.

Ascorbic acid, uric acid, and the like existing as ions in a neutral solution hardly passes through a hydrophobic layer, while neutral organic substances such as acetaminophen and the like do easily. In such case, a layer with a proper pore size is used not only to block an interferent of which molecular weight is large, but to have small molecules such as hydrogen peroxide and oxygen diffuse well.

There are small pores inside a layer of poly (phenylenediamine) poly(aminohydroxybenzene) or poly (dihydroxybenzene) which is formed by using monomers such as phenylenediamine owing to stacking among benzene rings in the polymer. A layer synthesized with meta-phenylenediamine or 2,3-diaminonaphthalene shows an excellent selectivity(Anal. Chem. 1998, 70, 2928).

However, interference of obstructive substances takes place greatly in a polymer layer containing enzymes which are polymerized electrochemically in a solution which also contains enzymes, which is because the obstructive substances move with ease through the vacant spaces inside the layer having the enzyme of which molecular weight is heavy.

A method of eliminating the interference in a glucose sensor is disclosed in Analytical Chemistry (Vol.66, 7th) In the method, the glucose sensor comprises an inner layer which works as a permselective layer for hydrogen peroxide, a middle layer in which an enzyme is immobilized, and an outer layer which has oxygen diffuse with ease but makes the diffusion of glucose slow. According to such method, the interference is eliminated by forming a nonconducting polymer layer on the inner layer by dip coating or electropolymerization, then, by falling a drop containing glucose oxidase thereon.

The above method enables fabrication of the sensor with ease when a relatively large electrode is introduced as well as elimination of the interference easily. But, the sensitivity of the sensor is reduced due to the decreasing amount of hydrogen peroxide transferred to the electrode since a nonconducting polymer layer formed by dip coating is thicker than the nonconducting polymer layer formed by electropolymerization.

SUMMARY OF THE INVENTION

Accordingly, the disclosed embodiments of the present invention are directed to an enzyme electrode sensor and a fabricating method thereof that substantially obviate one or more of the problems due to limitations and disadvantages of the related art.

The embodiments of the present invention provide an enzyme electrode sensor and a fabricating method thereof that reduces the interference of organic materials greatly by forming a nonconducting polymer layer containing enzymes by electropolymerization, then by forming another nonconducting polymer layer by electropolymerization.

Additional features and advantages of the invention will be set forth in the description that follows and in part will be apparent from the description, or may be learned by practice of the invention. The objectives and other advantages of the invention will be realized and attained by the structure particularly pointed out in the written description and the claims herein as well as the appended drawings.

To achieve these and other advantages and in accordance with the purpose of the present invention, as embodied and broadly described, the present invention includes an electrode, a first nonconducting polymer layer formed by electrochemical polymerization outside the electrode wherein enzyme is fixed to the nonconducting polymer layer, a second nonconducting polymer layer to which enzyme is not fixed, the second nonconducting layer formed by electrochemical polymerization outside the first nonconducting polymer layer, and an outer layer formed outside the second nonconducting layer. The electrode is a Pt electrode or a Rh electrode, and the enzyme is one of glucose oxidase, lactate oxidase, alcohol oxidase, cholesterol oxidase. The nonconducting polymer layers are formed one of poly (phenylenediamine), poly(aminohydroxybenzene), poly (dihydroxybenzene), poly(diamononaphthalene), poly (aminohydroxynaphthalene) and poly (dihydroxynaphthalene). The outer layer is formed one of polyurethane, cellulose acetate, Nafion, Teflon, Kel-F.

In another aspect, the present invention includes the steps of preparing an electrode, preparing a buffer solution containing monomers needed for forming a polymer layer and an enzyme, forming a first nonconducting polymer layer outside the electrode by electropolymerization wherein the enzyme is immobilized in the first nonconducting polymer layer and wherein a predetermined voltage is applied to the electrode in the buffer solution until a predetermined electric charge flows, washing the first nonconducting polymer layer with distilled water, forming a second nonconducting polymer layer outside the first nonconducting polymer layer by electropolymerization wherein the enzyme is not immobilized in the second nonconducting polymer layer, washing the second nonconducting polymer layer with distilled water, forming an outer layer outside the second nonconducting polymer layer, and drying the outer layer.

In the method, the enzyme is one of glucose oxidase, lactate oxidase, alcohol oxidase, cholesterol oxidase, the nonconducting polymer layers are formed one of poly (phenylenediamine), poly(aminohydroxybenzene), poly (dihydroxybenzene), poly(diamononaphthalene), poly (aminohydroxynaphthalene) and poly (dihydroxynaphthalene), and the outer layer is formed one of polyurethane, cellulose acetate, Nafion, Teflon, Kel-F.

It is to be understood that both the foregoing general description and the following detailed description are exemplary and explanatory and are intended to provide further explanation of the invention as claimed.

BRIEF DESCRIPTION OF THE DRAWINGS

The embodiments of the present invention will be explained with reference to the accompanying drawings, in which:

The accompanying drawings, which are included to provide a further understanding of the invention and are incorporated in and constitute a part of this application, illustrate embodiments of the invention and together with the description nerve to explain the principle of the invention.

In the drawings:

FIG. 1 shows partially a cross-sectional view of an enzyme electrode sensor according to the present invention;

FIG. 2 and FIG. 3 show cyclic voltammograms in an ascorbic acid solution; and

FIG. 4 and FIG. 5 show a cyclic voltammograms in an acetaminophene solution.

DETAILED DESCRIPTION OF THE INVENTION

Figure 1:
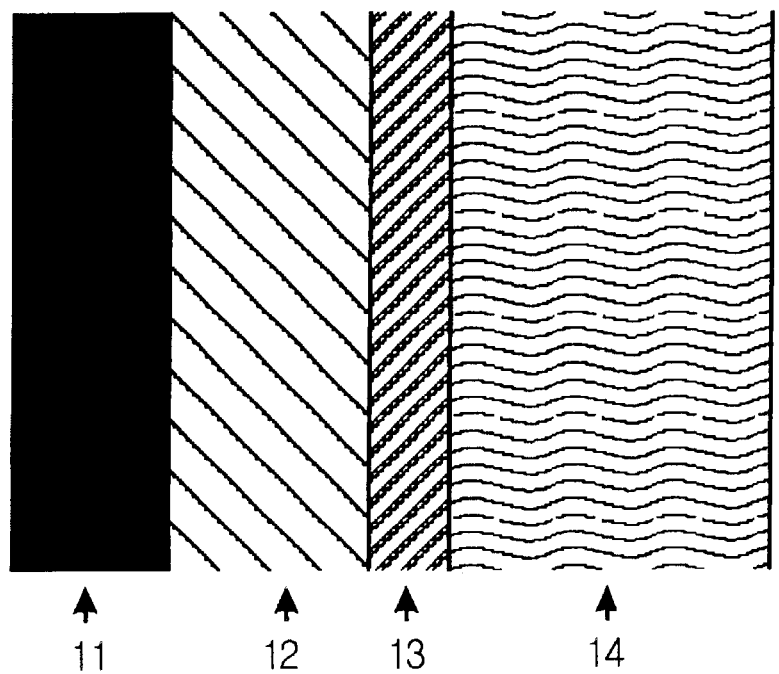

Reference will now be made in detail to the preferred embodiments of the present invention, examples of which are illustrated in the accompanying drawings.

An enzyme electrode sensor according to the present invention consists of a nonconducting polymer layer formed on the surface of an electrode by electrochemical polymerization wherein the enzymes are fixed to the nonconducting polymer layer, the other nonconducting polymer layer formed on the nonconducting polymer layer to which the enzymes are fixed wherein the other nonconducting polymer layer is formed by electrochemical polymerization and wherein enzymes are not fixed to the other nonconducting polymer layer, and an outer layer formed outside the other nonconducting polymer layer.

One of Pt and Rh electrodes is used as an electrode of the enzyme electrode sensor, and a nonconducting polymer layer to which enzymes are fixed by electrochemical polymerization is formed on the electrode.

In order to form a polymer layer, monomers for the polymer and a buffer solution containing enzymes to be used are prepared. In this case, an acetate buffer solution is preferred as the buffer solution.

Once the electrode is immersed in the buffer solution while a predetermined voltage is applied to the electrode until a fixed current is achieved, a nonconducting polymer layer to which enzymes are fixed is formed outside the electrode by electrochemical polymerization. Washing is carried out by distilled water after the polymer layer has been formed.

In this case, the enzymes may include glucose oxidase, lactate oxidase, alcohol oxidase, cholesterol oxidase, or the like.

One of poly(phenylenediamine), poly(aminohydroxybenzene), poly(dihydroxybenzene), poly(diamononaphthalene), poly(aminohydroxynaphthalene) and poly(dihydroxynaphthalene) is preferred for the basic substance of forming the nonconducting polymer layer electrochemically.

The other nonconducting polymer layer containing no enzyme is formed by electrochemical polymerization on the previous nonconducting polymer layer to which the enzymes are fixed.

The other nonconducting polymer layer is formed by immersing the electrode, on which the nonconducting polymer layer in which the enzymes are immobilized, to which a predetermined voltage is applied for a predetermined time in a buffer, acid, and Nafion solution wherein monomers are contained in the solution.

Alternatively, the other nonconducting polymer layer may be formed by immersing the electrode, on which is the nonconducting polymer layer in which the enzymes are immobilized, in a buffer solution containing no monomer, by applying a predetermined voltage to the electrode for a predetermined time, then by immersing the electrode to which predetermined voltage is applied for a predetermined time again in a buffer, acid, and Nafion solution wherein monomers are contained in the solution.

An electropolymerization takes place during the above procedures, thereby forming a nonconducting polymer layer again outside the nonconducting polymer layer in which the enzymes are immobilized. Then, the newly-formed polymer layer is washed by distilled water.

In this case, it is desirable to use a mixed solution which includes a PBS(phosphate buffered saline) solution, an acid solution, and a mixed solution of water and alcohol in which Nafion is dissolved to prepare the solution. And, one of poly(phenylenediamine), poly(aminohydroxybenzene), poly(dihydroxybenzene), poly(diamononaphthalene), poly(aminohydroxynaphthalene) and poly(dihydroxynaphthalene) is preferred for the basic substance of forming the nonconducting polymer layer electrochemically.

An outer layer is formed outside the nonconducting polymer layer. The outer layer is formed by coating the electrode on which is the nonconducting polymer layers with a solution containing the substantial substance of the outer layer, wherein the enzymes are immobilized in one of the nonconducting layers. The substance for forming the outer layer is preferably one of polyurethane, cellulose, acetate, Nafion, Teflon, and Kel-F.

An enzyme electrode sensor is completed by drying the outer layer. In this case, the step of drying is preferably carried out at a vacuum state.

FIG. 1 shows partially a cross-sectional view of an enzyme electrode sensor according to the present invention.

Referring to FIG. 1, an enzyme electrode sensor according to the present invention includes an electrode 11, a nonconducting polymer layer 12, which is formed by electropolymerization in which enzymes are immobilized, the other nonconducting polymer layer 13 formed by electropolymerization, and an outer layer 14.

Reference will now be made in detail to the representative embodiments of the present invention. It will be apparent to those skilled in the art that various modifications and variations can be made in the present invention without departing from the spirit or scope of the inventions.

EXAMPLE 1

An electrochemical polymerization is carried out by immersing a Pt electrode in an acetate buffer solution containing 5 mM meta-phenylenediamine and 250 unit/ml glucose oxidase and by applying 0.7 V to the Pt electrode until electric charges of 7.5 $mC/cm^2$ flows, wherein an Ag/AgCl reference electrode is taken as a criterion.

After the reaction has been completed, the electrode is washed by distilled water. Then, the electrode is put into a PBS(phosphate buffered saline) solution of which pH is 7.4, to which 1.0 V is applied for 10 minutes.

Having been washed again by distilled water, the electrode is dip-coated in a 2.5 wt/% Nafion solution. Then, the electrode is dried for 20 minutes at a vacuum state.

EXAMPLE 2

An electrochemical polymerization is carried out by immersing a Pt electrode in an acetate buffer solution(pH 5.6) containing 5 mM meta-phenylenediamine and 250 unit/ml glucose oxidase and by applying 0.7 V to the Pt electrode until electric charges of 7.5 $mC/cm^2$ flows, wherein an Ag/AgCl reference electrode is taken as a criterion.

After the reaction has been completed, the electrode is washed by distilled water. Then, the electrode is put into a PBS solution, to which 1.0 V is applied for 10 minutes. And, the electrode is put into a PBS solution containing 5 mM meta-phenylenediamine, to which 1.0 V is applied for 10 minutes.

Having been washed again by distilled water, the electrode is dip-coated in a 2.5 wt/% Nafion solution. Then, the electrode is dried for 20 minutes at a vacuum state.

EXAMPLE 3

An electrochemical polymerization is carried out by immersing a Pt electrode in an acetate buffer solution(pH 5.6) containing 5 mM meta-phenylenediamine and 250 unit/ml glucose oxidase and by applying 0.7 V to the Pt electrode until electric charges of 7.5 $mC/cm^2$ flows, wherein an Ag/AgCl reference electrode is taken as a criterion.

After the reaction has been completed, the electrode is washed by distilled water. Then, the electrode is put into a solution of 5 mM 2,3-diaminonaphthalene, 0.1 M HCl and 0.2 M NaCl, to which 1.0 V is applied for 10 minutes.

Having been washed again by distilled water, the electrode is dip-coated in a 2.5 wt/% Nafion solution. Then, the electrode is dried for 20 minutes at a vacuum state.

EXAMPLE 4

An electrochemical polymerization is carried out by immersing a Pt electrode in an acetate buffer solution(pH 5.6) containing 5 mM meta-phenylenediamine and 250 unit/ml glucose oxidase and by applying 0.7 V to the Pt electrode until electric charges of 7.5 $mC/cm^2$ flows, wherein an Ag/AgCl reference electrode is taken as a criterion.

After the reaction has been completed, the electrode is washed by distilled water. Then, the electrode is put into a water solution of 5 mM 2,3-diaminonaphthalene, 0.5 wt % Nafion and 10 wt % methanol, to which 1.0 V is applied for 10 minutes.

Having been washed again by distilled water, the electrode is dip-coated in a 2.5 wt/% Nafion solution. Then, the electrode is dried for 20 minutes at a vacuum state.

EXAMPLE 5

An electrochemical polymerization is carried out by immersing a Pt electrode in an acetate buffer solution(pH 5.6) containing 5 mM meta-phenylenediamine and 250 unit/ml lactate oxidase and by applying 0.7 V to the Pt electrode until electric charges of 7.5 $mC/cm^2$ flows, wherein an Ag/AgCl reference electrode is taken as a criterion.

After the reaction has been completed, the electrode is washed by distilled water. Then, the electrode is put into a PBS solution, to which 1.0 V is applied for 10 minutes. And, the electrode is put into a PBS solution containing 5 mM meta-phenylenediamine, to which 1.0 V is applied for 10 minutes.

Having been washed again by distilled water, the electrode is dip-coated in a 2.5 wt/% Nafion solution. Then, the electrode is dried for 20 minutes at a vacuum state.

EXAMPLE 6

An electrochemical polymerization is carried out by immersing a Pt electrode in an acetate buffer solution(pH 5.6) containing 5 mM meta-phenylenediamine and 250 unit/ml glucose oxidase and by applying 0.7 V to the Pt electrode until electric charges of 7.5 $mC/cm^2$ flows, wherein an Ag/AgCl reference electrode is taken as a criterion.

After the reaction has been completed, the electrode is washed by distilled water. Then, the electrode is put into a PBS solution, to which 1.0 V is applied for 10 minutes. And, the electrode is put into a PBS solution containing 5 mM meta-phenylenediamine, to which 1.0 V is applied for 10 minutes.

Having been washed again by distilled water, the electrode is dip-coated in a 2.5 wt/% Nafion solution. Then, the electrode is dried for 20 minutes at a vacuum state.

EXAMPLE 7

An electrochemical polymerization is carried out by immersing a Pt electrode in an acetate buffer solution(pH 5.6) containing 5 mM meta-phenylenediamine and 250 unit/ml glucose oxidase and by applying 0.7 V to the Pt electrode until electric charges of 7.5 $mC/cm^2$ flows, wherein an Ag/AgCl reference electrode is taken as a criterion.

After the reaction has been completed, the electrode is washed by distilled water. Then, the electrode is put into a PBS solution, to which 1.0 V is applied for 10 minutes. And, the electrode is put into a PBS solution containing 5 mM meta-phenylenediamine, to which 1.0 V is applied for 10 minutes.

Having been washed again by distilled water, the electrode is dip-coated in a 2.5 wt/% Nafion solution. Then, the electrode is dried for 20 minutes at a vacuum state.

Then, the electrode is dip-coated twice in a 0.4 wt/% polyurethane solution. And, the electrode is dried for 20 minutes at a vacuum state.

Experiment 1

The interference of ascorbic acid which is the obstructive substance is examined after and before a Pt electrode is coated with a poly(meta-phenylenediamine).

The degree of interference is measured in a PBS buffer solution, in which 10 mM ascorbic acid is dissolved, by a cyclic voltammogram obtained at a scan rate of 10 mV/sec for a Pt electrode, a Pt electrode on which a poly(meta-phenylenediamine) layer is formed only wherein glucose oxidase is immobilized in the poly(meta-phenylenediamine) layer, and a Pt electrode on which a poly(meta-phenylenediamine) layer in which glucose oxidase is immobilized and the other poly(meta-phenylenediamine) layer are formed successively.

Figure 2:
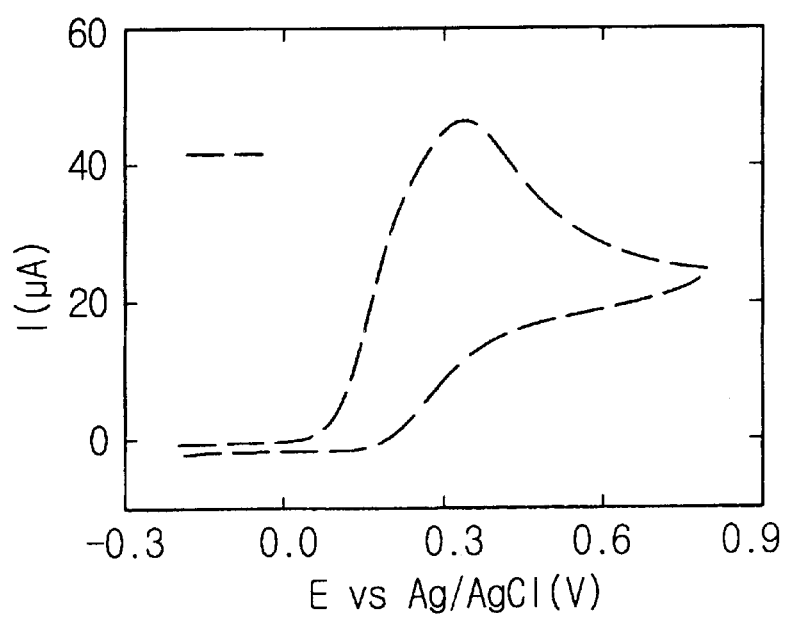
Figure 3:
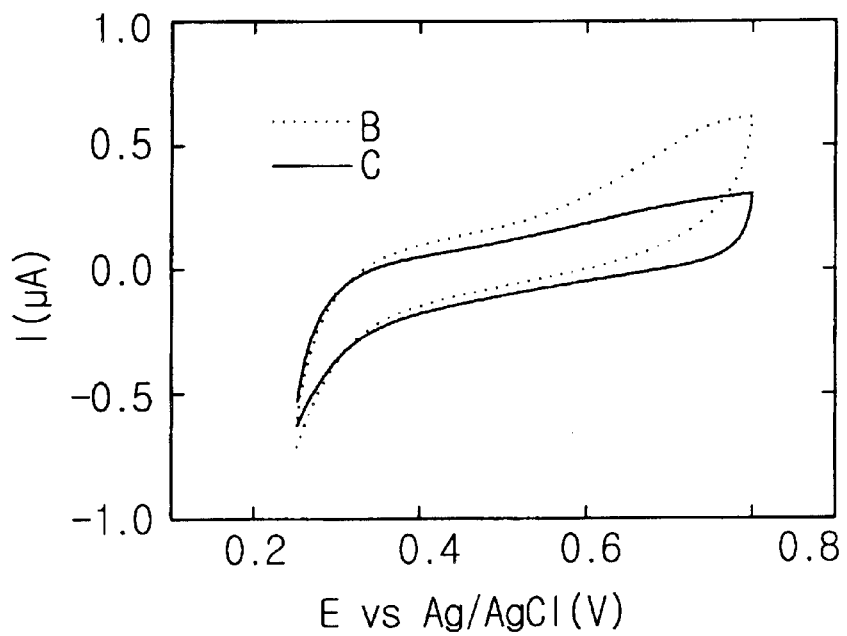

The results of the measurement are shown in FIG. 2 and FIG. 3.

Graph A in FIG. 2 shows a result of a Pt electrode of reference, illustrating that oxidation of ascorbic acid takes place preferably under 650 mV.

Graph B in FIG. 3 shows a result of a Pt electrode on which a poly(meta-phenylenediamine) layer is formed only wherein glucose oxidase is fixed to the poly(meta-phenylenediamine) layer, illustrating that current is reduced abruptly but that there still exists the influence of ascorbic acid.

Graph C in FIG. 3 shows a result of a Pt electrode on which a poly(meta-phenylenediamine) layer and the other poly(meta-phenylenediamine) layer to which glucose oxidase is fixed are formed successively, illustrating that the influence of ascorbic acid is insignificant.

Namely, in the solution in which ascorbic acid is dissolved, maximum oxidizing current is reduced to 46A, 0.62A, and 0.31A corresponding to the Pt electrode, the Pt electrode coated with a nonconducting polymer layer, and the Pt electrode coated with two polymer layers. Thus, the maximum oxidizing current is reduced to less than 1/100.

Considering that maximum current is about 0.12 $\mu$A, the interference effect of ascorbic acid on the Pt electrode coated with two polymer layers is insignificant.

Experiment 2

The interference of ascorbic acid which is the obstructive substance is examined after and before a Pt electrode is coated with a poly(meta-phenylenediamine).

The degree of interference is measured in a PBS buffer solution, in which 10 mM acetaninophen is dissolved, by a cyclic voltammogram obtained at a scan rate of 10 mV/sec for a Pt electrode, a Pt electrode on which a poly(meta-phenylenediamine) layer is formed only wherein glucose oxidase is immobilized in the poly(meta-phenylenediamine) layer, and a Pt electrode on which a poly(meta-phenylenediamine) layer in which glucose oxidase is immobilized and the other poly(meta-phenylenediamine) layer are formed sucessively.

Figure 4:
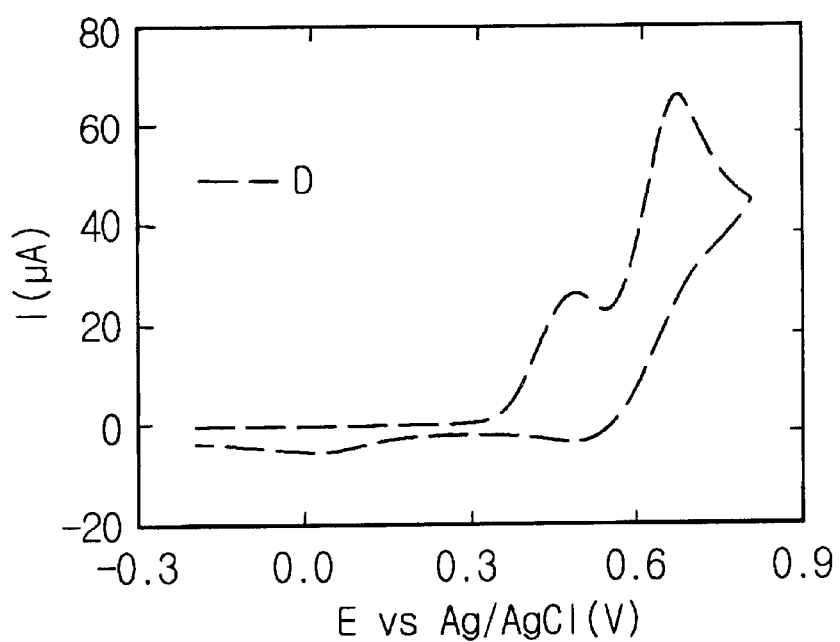
Figure 5:
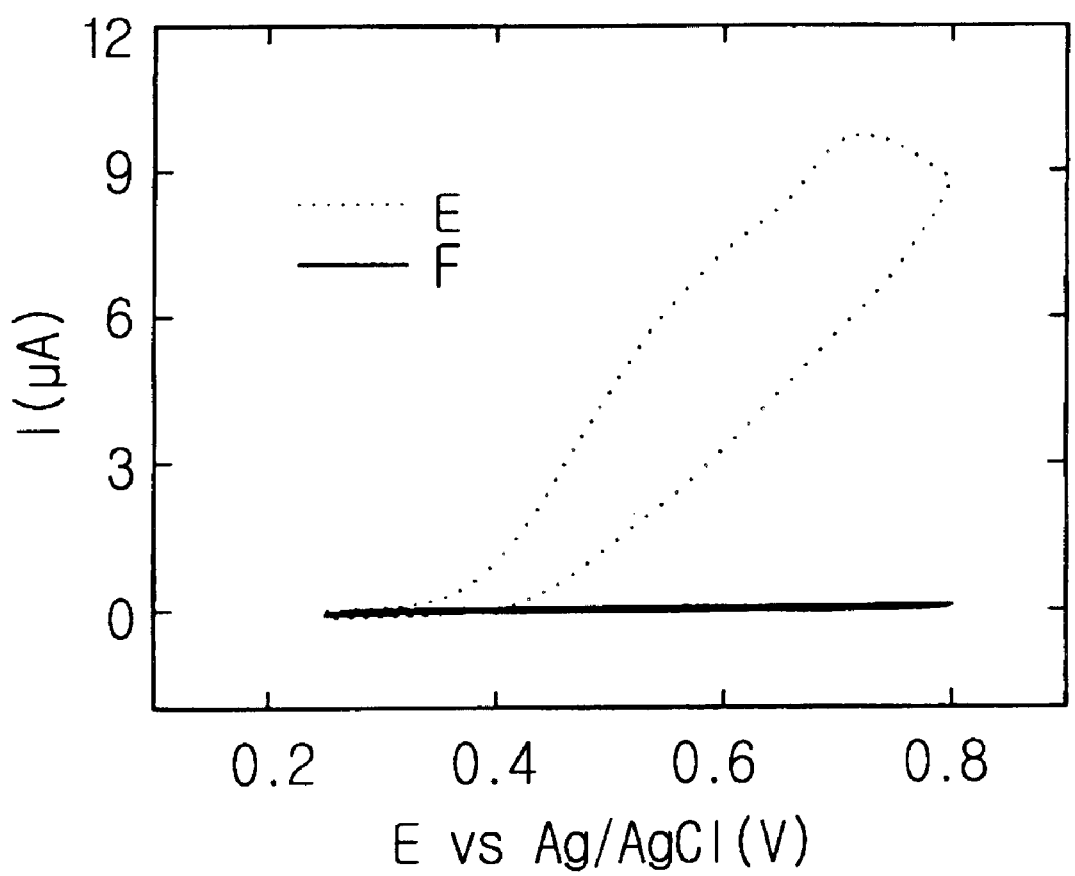

The results of the measurement are shown in FIG. 4 and FIG. 5.

Graph D in FIG. 4 shows a result of a Pt electrode of reference, illustrating that oxidation of acetaminophene acid takes place preferably under 650 mV as well.

Graph E in FIG. 5 shows a result of a Pt electrode on which a poly(meta-phenylenediamine) layer is formed only wherein glucose oxidase is fixed to the poly(meta-phenylenediamine) layer, illustrating that current is reduced abruptly but that oxidizing current of aetaminophene is relatively large.

Graph F in FIG. 5 shows a result of a Pt electrode on which a poly(meta-phenylenediamine) layer and the other poly(meta-phenylenediamine) layer to which glucose oxidase is fixed are formed successively, illustrating that oxidizing current of acetaminophene is insignificant.

Namely, in the solution in which acetaminophen is dissolved, maximum oxidation current is reduced to 67 $\mu$A) 9.7 $\mu$A, and 0.12 $\mu$A corresponding to the Pt electrode, the Pt electrode coated with a nonconducting polymer layer, and the Pt electrode coated with two polymer layers, respectively. Thus, the maximum oxidation current is reduced to under 1/100.

Considering that maximum current is about 0.12A, interference effect of acetaminophene on the Pt electrode coated with two polymer layers is insignificant.

The enzyme electrode sensor of the present invention enables application to a blood sugar sensor and biosensors using different enzymes as well as to the fabrication of a small-sized multi-functional sensor for inspecting human health. Particularly, the present invention enables application to a microsensor system which may be built in or attached to a human body for long-term use.

As an inner layer is formed by electropolymerization and enzyme is fixed, the present invention may be used to fabricate a microsensor that cannot introduce dip coating or spin coating as well as to form micro patterns of a sensing layer of a micro-array electrode which can detect various substances simultaneously.

It will be apparent to those skilled in the art that various modifications and variations can be made in an enzyme electrode sensor and a fabricating method thereof of the present invention without departing from the spirit or scope of the inventions. Thus, it is intended that the present invention covers the modifications and variations of this invention provided they come within the scope of the appended claims and their equivalents.

What we claim:

1. An enzyme electrode sensor, comprising:

an electrode;

a first electropolymerized nonconducting polymer layer formed outside the electrode;

a second electropolymerized nonconducting polymer layer formed outside the first electropolymerized nonconducting polymer layer;

an outer layer formed outside the second electropolymerized nonconducting polymer layer; and enzyme fixed to the first electropolymerized nonconducting polymer layer, and no enzyme fixed to the second electropolymerized nonconducting polymer layer.

2. The enzyme electrode sensor of claim 1 wherein the electrode is one of either a Pt electrode and an Rh electrode.

3. The enzyme electrode sensor of claim 1 wherein the enzyme is one of either glucose oxidase, lactate oxidase, alcohol oxidase, and cholesterol oxidase.

4. The enzyme electrode sensor of claim 1 wherein the first and second electropolymerized nonconducting polymer layers comprise one of either poly(phenylenediamine), poly(aminohydroxybenzene), poly(dilhydroxybenzene) poly(diamnononaphthalene), poly(aminohydroxynaphthalene), and poly(dihycroxynaphthalene).

5. The enzyme electrode sensor of claim 1 wherein the outer layer comprises one of either polyurethane, cellulose acetate, Nafion, Teflon, and Kel-F.

6. An enzyme electrode sensor, comprising:

an electrode;

a first nonconducting polymer layer formed by electrochemical polymerization outside the electrode wherein an enzyme is fixed to the nonconducting polymer layer;

a second nonconducting polymer layer to which the enzyme is not fixed, the second nonconducting layer formed by electrochemical polymerization outside the first nonconducting polymer layer; and an outer layer formed outside the second nonconducting layer, the nonconducting polymer layers comprising one of either poly(phenylenediamine), poly(aminohydroxybenzene), poly(dihydroxybenzene), poly(diamononaphthalene), and poly(aminohydroxynaphthalene), and poly(dihydroxynaphthalene).

* * * * *